(12) United States Patent
Thabeth et al.

(10) Patent No.: US 9,116,102 B2
(45) Date of Patent: Aug. 25, 2015

(54) IMAGING APPARATUS

(75) Inventors: Khalid Thabeth, Newtownabbey (GB); Frank Lunney, Belfast (GB); Turan Mirza, Lisburn (GB)

(73) Assignee: Advanced Sensors Limited, Carrickfergus, County Antrim (GB)

( * ) Notice: Subject to any disclaimer, the term of this patent is extended or adjusted under 35 U.S.C. 154(b) by 324 days.

(21) Appl. No.: 13/640,671

(22) PCT Filed: Apr. 14, 2011

(86) PCT No.: PCT/EP2011/055909
§ 371 (c)(1),
(2), (4) Date: Oct. 26, 2012

(87) PCT Pub. No.: WO2011/128406
PCT Pub. Date: Oct. 20, 2011

(65) Prior Publication Data
US 2013/0235189 A1    Sep. 12, 2013

(30) Foreign Application Priority Data
Apr. 14, 2010    (GB) .................................. 1006180.2

(51) Int. Cl.
*G01N 21/17*    (2006.01)
*G01N 21/35*    (2014.01)
(Continued)

(52) U.S. Cl.
CPC ................ *G01N 21/17* (2013.01); *B08B 7/028* (2013.01); *G01N 15/0227* (2013.01);
(Continued)

(58) Field of Classification Search
CPC .......... B01J 19/08; B01D 17/06; G02B 5/10; B23K 26/02; C40B 30/06; C40B 60/12; A61B 6/00; G01N 21/45

USPC .................. 348/135; 427/596; 73/570, 432.1; 359/859, 731; 219/121 LV; 506/10; 600/436; 422/82.05
See application file for complete search history.

(56) References Cited

U.S. PATENT DOCUMENTS 4,707,585 A * 11/1987 Monteith et al. ......... 219/121.79
5,831,166 A * 11/1998 Kozuka et al. .................. 73/570
(Continued)

OTHER PUBLICATIONS

Yuk et al ("Development of a scanning surface plasmon microscope based on white light for analysis of a wide range of protein arrays", Sensors and Actuators B, vol. 131. No. 1, Apr. 14, 2008, pp. 241-246, XP022602890, Elseivier Sequoia S.A., Lausanne, CH, ISSN: 0925-4005, DOI: 10.1016/J.SNB.2007.11.019).*

*Primary Examiner* — Sath V Perungavoor
*Assistant Examiner* — Patricia I Young
(74) *Attorney, Agent, or Firm* — Gunn, Lee & Cave, P.C.

(57) ABSTRACT

An apparatus for measuring oil droplets and other bodies in a liquid, the apparatus comprising a body having an imaging device mounted therein, said body having a measurement window adjacent a measuring region through which an image of a fluid within the measurement region may be viewed by the imaging device, wherein a light source is provided for illuminating said measurement region, said light source being directed towards the imaging device by a light directing means, the apparatus including an ultrasonic transducer mechanically coupled to the measurement window for removing fouling from the measurement window and for creating cavitation within said measurement region, wherein said light directing means is located in or adjacent said measurement region to be exposed to said cavitation created by the ultrasonic transducer to remove fouling from said light directing means.

4 Claims, 4 Drawing Sheets

(51) Int. Cl.

| | | |
|---|---|---|
| *B01D 17/06* | (2006.01) | |
| *B23K 26/02* | (2014.01) | |
| *B08B 3/00* | (2006.01) | |
| *F16F 9/04* | (2006.01) | |
| *B08B 7/02* | (2006.01) | |
| *G01N 15/02* | (2006.01) | |
| *G01N 21/15* | (2006.01) | |
| *G01N 21/64* | (2006.01) | |
| *G01N 15/00* | (2006.01) | |
| *G02B 1/02* | (2006.01) | |

(52) U.S. Cl.
CPC ............ *G01N 21/15* (2013.01); *G01N 21/6456* (2013.01); *G01N 2015/003* (2013.01); *G01N 2021/154* (2013.01); *G02B 1/02* (2013.01)

(56) References Cited

U.S. PATENT DOCUMENTS

| | | | |
|---|---|---|---|
| 6,142,641 A * | 11/2000 | Cohen et al. | 359/859 |
| 6,637,733 B1 * | 10/2003 | Weitzenhof et al. | 267/64.27 |
| 6,643,538 B1 * | 11/2003 | Majewski et al. | 600/436 |
| 2004/0065830 A1 * | 4/2004 | Boon et al. | 250/339.11 |
| 2005/0081893 A1 * | 4/2005 | Nilsen | 134/34 |
| 2009/0042737 A1 * | 2/2009 | Katz et al. | 506/10 |
| 2009/0074988 A1 * | 3/2009 | Faris et al. | 427/596 |

* cited by examiner

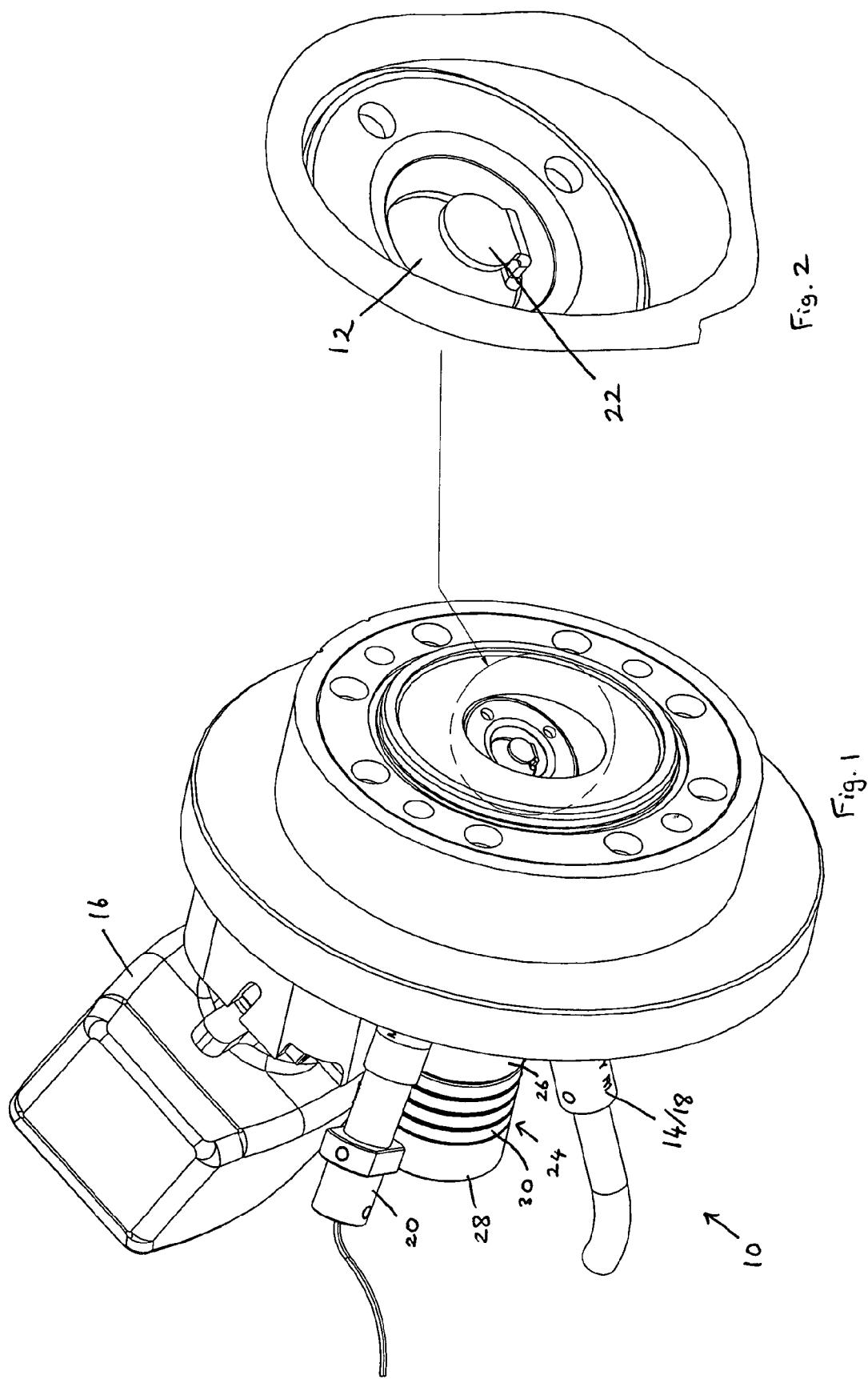

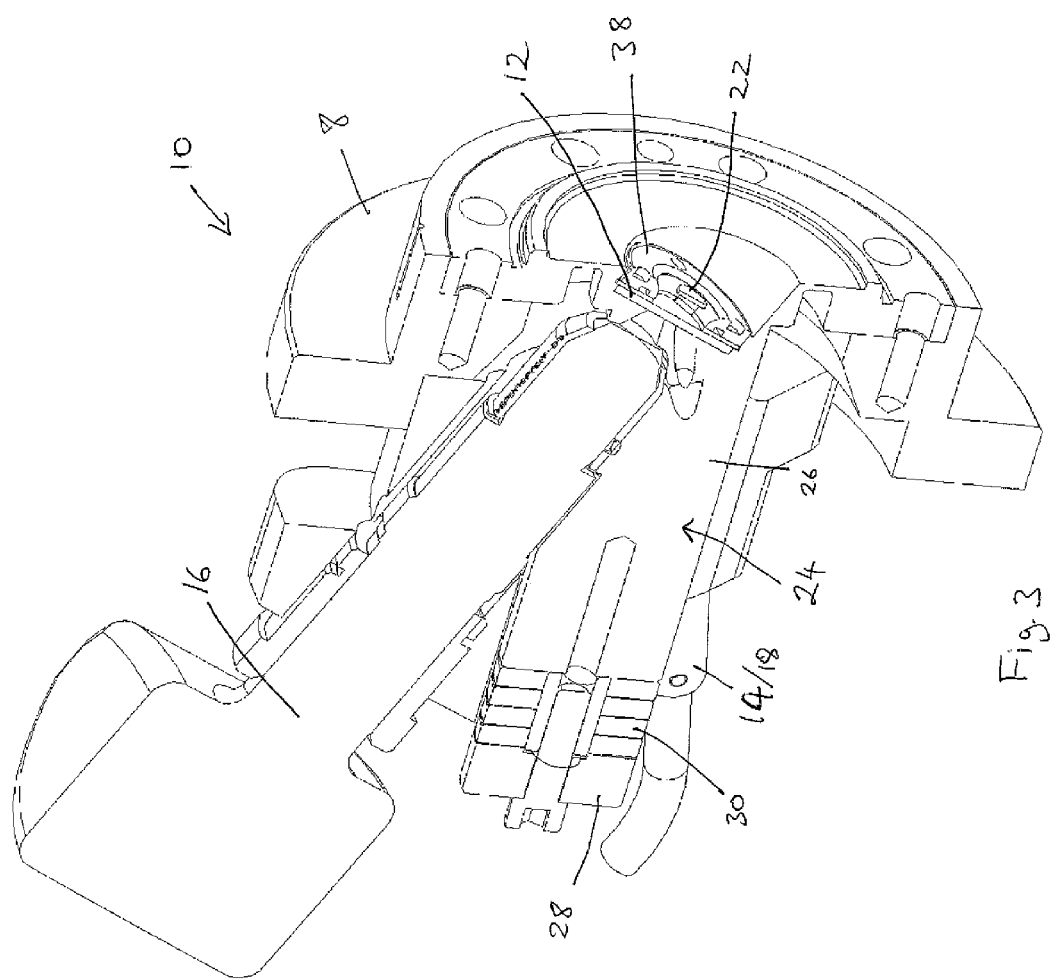

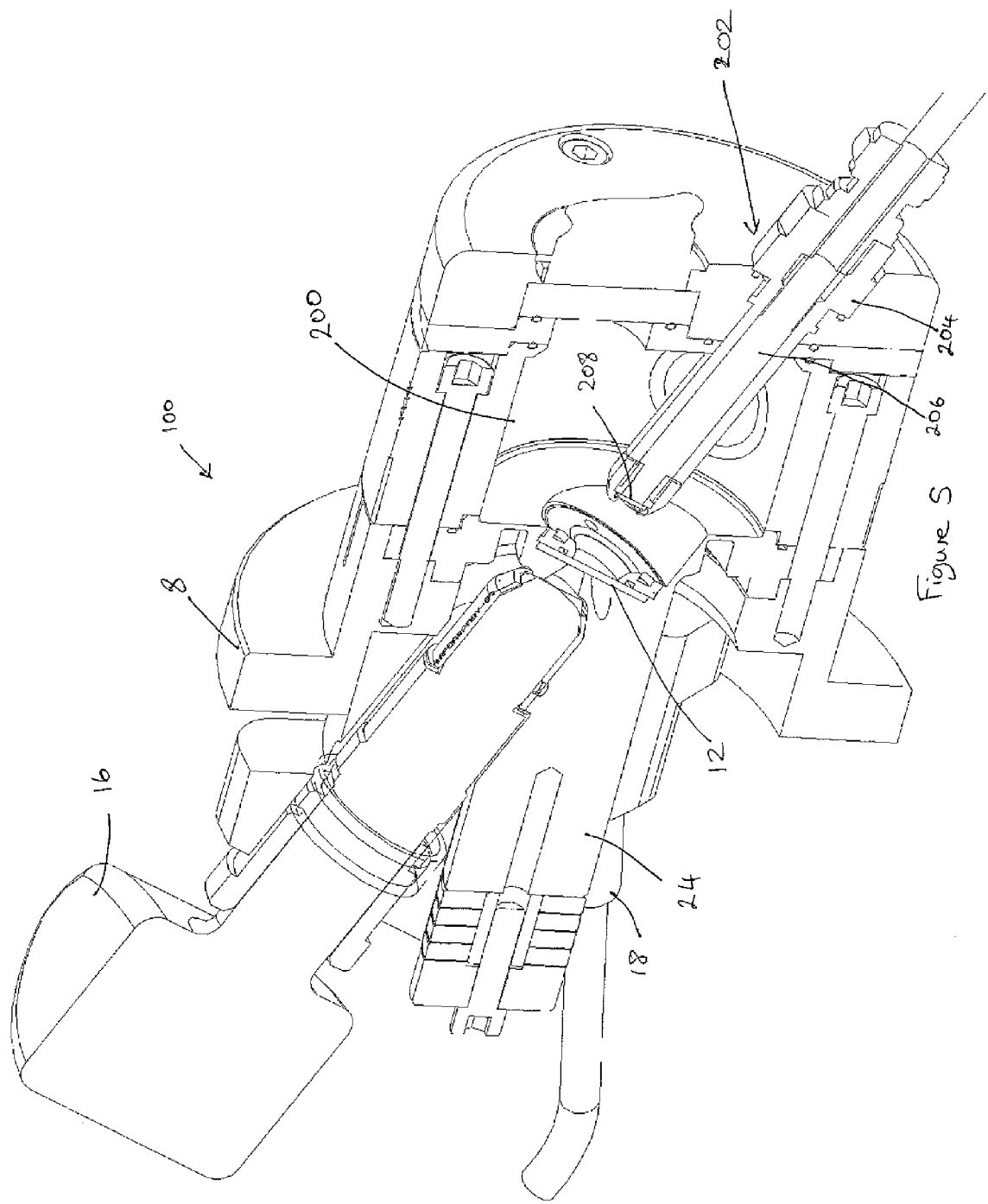

IMAGING APPARATUS

This invention relates to an imaging apparatus for the measurement of oil droplet and other bodies in a liquid, particularly water, and in particular a self cleaning optical window for the lighting and image to pass through.

There are many applications that require measurement of the concentration or quantity of oil that is present in a liquid. For example, in pipes leading from oil production or refining facilities it may be required to measure the amount of oil that is present in the liquid (mainly water) flowing in the pipes. To this end it is known to provide an in-line or side stream measurement apparatus which measures the amount of oil that is present.

Oil has a natural fluorescence. Therefore, commonly, such measurement apparatus measures the quantity of oil by the detection of fluorescence. Devices that detect and/or measure fluorescence are commonly referred to as fluorometers. A fluorometer usually includes a light source, such as a laser, to cause fluorescence in the oil and a detector with spectral analysis to detect the fluorescing oil droplets. A typical fluorometer has a window, forming a wall of a measurement chamber, through which the excitation light source is transmitted into said measurement chamber and through which the resultant fluorescent light is received by the fluorometer. Such devices are extremely effective at detecting the concentration of oil in a water sample, which may be a sealed water sample or flowing water.

However, fluorometers are not effective at analyzing the sample, in particular measuring the size of the oil droplets (and other bodies) in the water. A better way to do this is to use an imaging device, such as a camera, to take images of the sample. These images can then be analysed and the size, size distribution and quantity of the oil droplets, and other foreign bodies in the water can be determined. This process is often referred to as microscopy or video microscopy. It is also known to use microscopy to determine the amount of oil in the water in parts per million.

For microscopy techniques to be used to analyse oil in water, the water sample (target bodies) requires lighting, the sample can be lit from the front or the side, lighting may also be achieved by providing a backlight at one side of the sample and an imaging device at the other side of the sample, the imaging device typically being located behind a viewing window.

An alternative is to provide a mirror on an opposite side of the viewing window from the imaging device and to provide a light source adjacent the camera for projecting light towards the mirror to be reflected towards the camera. This also enables the mirror to define a small sampling region between the mirror and the viewing window and is therefore potentially applicable to in-line oil measurement. However, all lighting sources including the mirror require them to be exposed to the fluid being viewed and thus they become prone to contamination from oil and other contaminants in such fluid.

This problem may be addressed by using an ultrasonic device to clean the window. Prior art systems such techniques have not been able to overcome the problems of fouling of the light source window or viewing window.

According to the present invention there is provided an apparatus for measuring oil droplets and other bodies in a liquid, the apparatus comprising a body having an imaging device mounted therein, said body having a measurement window adjacent a measuring region through which an image of a fluid within the measurement region may be viewed by the imaging device, wherein a light source is provided for illuminating said measurement region, said light source being directed towards the imaging device by a light directing means, the apparatus including an ultrasonic transducer mechanically coupled to the measurement window for removing fouling from the measurement window and for creating cavitation within said measurement region, wherein said light directing means is located in or adjacent said measurement region to be exposed to said cavitation created by the ultrasonic transducer to remove fouling from said light directing means.

Said light directing means may comprise a window through which light from the light source is transmitted, a light guide through which said light is transmitted, such as an optical cable, or a mirror located adjacent said viewing window for reflecting light from the light source towards the imaging device.

Preferably said body comprises or incorporates an elongate ultrasonic transducer comprising one or more ceramic transducer elements and a reaction mass mounted against said one or more ceramic transducer elements at a first end of said body, said measurement window being provided at a second end of said elongate member, opposite said first end.

Preferably the measurement window, at least in the regions through which through which light passes from the light source to the imaging device, is positioned, angled or otherwise shaped or profiled such that said light passes through the window perpendicular to the said surfaces of the window to prevent diffraction of said light by the window. In one embodiment the measurement window is mounted perpendicular to a longitudinal axis of the imaging device. Alternatively the measurement window may be mounted perpendicular to a longitudinal axis of the ultrasonic transducer and the region of the window through which light passes to the imaging device may be shaped or cut such that the surfaces of such region extend perpendicular to the longitudinal axis of the imaging device.

Preferably the window is formed from a sapphire disc to withstand the ultrasonic cavitations created by the ultrasonic cleaning activity.

In one embodiment said light source is mounted within or adjacent said body to direct light through said measurement window into said measurement region, a mirror being provided within said measurement region externally of said window for reflecting light from the light source towards the imaging device. Preferably both the measurement window and the mirror are mechanically coupled to said ultrasonic transducer to remove fouling from both the window and mirror.

Preferably said mirror is attached to or is mounted on said body to be mechanically coupled the ultrasonic transducer.

Preferably said measurement region is defined between said mirror and said measurement window.

Preferably said light source and said imaging device are located on respective axes converging on said mirror.

Preferably said imaging device and light source are mounted in respective channels provided in said body, said channels converging in a direction towards the mirror.

Preferably said mirror is mounted on said second end of the body adjacent said measurement window. In a preferred embodiment said mirror comprises a base portion or ring held or clamped between said window and a retaining ring mounted on said second end of said body, and a mirror portion mounted on said base portion by one or more linking members. Preferably said base portion and mirror portion are integrally formed from a single material. In a preferred embodiment said mirror is formed from a metal material, such as stainless steel, chrome duplex, monel etc.

An excitation source, such as a laser, may be provided, preferably on or within said body, for transmitting an excitation signal through said window for, a fluorescence detector being provided for detecting a fluorescent response from a sample. Said excitation source may be mounted in parallel with, or may comprise, said light source. Where said excitation source is separate from said light source, both may be provided in a common channel in the body of the apparatus. Said fluorescence detector is preferably mounted in said body at a location offset from said imaging device, preferably offset from the mirror such the detector is not exposed to light from the excitation source and/or light source reflected from the mirror.

In one embodiment said imaging device and light source may be arranged in a first plane extending through a longitudinal axis of the ultrasonic transducer and said fluorescence detector is arranged in a second plane extending through said longitudinal axis of said ultrasonic transducer, said second plane being circumferentially offset from said first plane, said mirror being arranged to reflect light from the light source to the imaging device in said first plane.

In a second embodiment, the light source is provide remote from said body, light from the light source being directed towards said imaging device via said light directing means. Said light directing means may comprise a window and/or a light guide, wherein said window and/or a terminal end of said light guide is located within or adjacent said measurement region to be exposed to the cavitation generated by the ultrasonic transducer to remove fouling therefrom.

In a preferred embodiment said light directing means comprises a light guide in the form of an optical cable. The light guide may extend within an elongate body extending into said measurement region.

Said light guide may terminate in a window mounted in a distal end of the elongate body, said window being exposed to the cavitation generated by the ultrasonic transducer.

Thus an imaging apparatus in accordance with an embodiment of the present invention may incorporate both the laser/spectral analysis functionality of fluorometers with the additional functionality of a video microscopy apparatus so the amount of oil present can be measured by fluoroscopy and the size and composition of the oil droplets and other bodies can be analysed by video microscopy using a single apparatus.

Embodiments of the present invention will now be described, by way of example only, with reference to the accompanying drawings, in which:—

FIG. 1 is a perspective view of an imaging apparatus according to an embodiment of the present invention;

FIG. 2 is a detailed view of a measurement window portion of the apparatus of FIG. 1;

FIG. 3 is a sectional view through the apparatus of FIG. 1;

FIG. 5 is a sectional view of an imaging device according to a second embodiment of the present invention.

Figure 4:
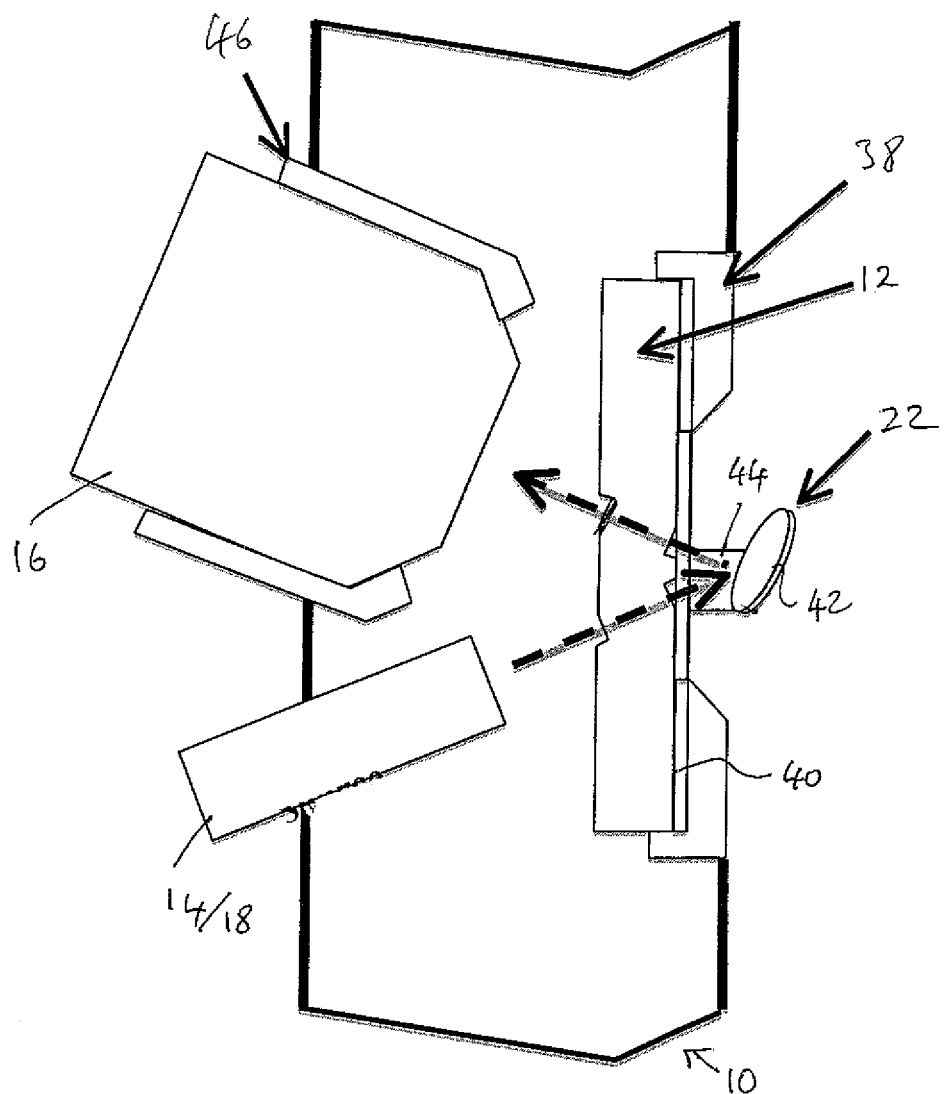
FIG. 4 is a schematic sectional view through the apparatus of FIG. 1 showing the alignment of the light source, camera and mirror.

Referring to the drawings, there is shown an apparatus, generally indicated as 10, for measuring the concentration of oil in water using fluorescence and analysing the size and composition of oil droplets and other foreign bodies in the water using video microscopy.

In particular, the apparatus 10 may be said to be an in-line measurement apparatus since it may be incorporated, in use, into a pipe or conduit through which a liquid flows. In the following description, the liquid is assumed to comprise water and the fluorescent material is assumed to comprise oil, although it will be understood that that the invention is not limited to these.

The apparatus 10 comprises a measurement head assembly coupled to a measurement chamber (not shown). The apparatus comprises a measurement window 12 preferably defining a wall portion of a measurement chamber (not shown), which may be provided by a portion of said pipe or conduit or by a section of pipe or conduit that is separately formed from the pipe or conduit but is adapted for in-line connection therewith using any suitable conventional connectors, or which may comprise a closed measurement chamber for receiving a fluid sample for side-stream measurement.

The measurement window 12 may be formed from any suitable transparent material which is capable of withstanding ultrasonic shock, e.g. sapphire crystal. The measurement chamber may also include a viewing window (not shown) that may allow the contents of the chamber to be viewed. The viewing window may be formed from any suitable transparent material, e.g. sapphire crystal or quartz; and may be provided with a cover or cap to obscure the window if required.

The measurement head assembly 8 includes a light source 14 and an imaging camera 16 for microscopy functions and an excitation source 18 (which may comprise a separate component or may be provided as a separate function of the light source 14), and a detector 20 for fluoroscopy functions.

In order to produce a backlight for microscopy, a stainless steel mirror 22 is mounted on the front of the measurement head assembly. The mirror is positioned to reflect the light from the light source 14 in the direction of the camera 16 and defines a measurement or sampling region between the mirror 22 and window 12.

As shown in FIG. 3, the measurement window 12 is mounted in the measurement head assembly 8 to extend perpendicular to the longitudinal axis of the imaging camera 16 to avoid the problem of diffraction of the light passing through the measurement window 12 from the mirror 22.

The excitation source 18 is arranged to direct an excitation signal through the measurement window 12 into the measurement chamber in order to cause fluorescence of the oil mixed with, or suspended in, the water. The detector 20 is arranged to receive or detect said fluorescence through the window 12.

The excitation source 18 may comprise means for emitting any signal that causes fluorescence in the target material. Typically, the excitation signal comprises a light signal of any suitable wavelength, including visible light, UV light and IR light. In the present embodiment, the excitation source 18 comprises a laser source, for example a 3 mW laser diode module of 405 nm wavelength. In one embodiment the light source 14 and the excitation source 18 may comprise a single light emitting means, such as a laser.

Advantageously, the detector 20 includes a light guide for collecting or receiving fluorescent light from the measurement chamber and guiding it to a photosensor or photodetector module. The light guide may comprises at least one optical fibre (or other optical conduit), but typically a plurality of optical fibres (or other conduits) packaged together, to provide an optical transmission channel by which light may be directed to the photosensor. A light guide may also be referred to as an optical cable and may comprise a bundle of one or more individual optical cables, wires or the like.

The detector 20 is mounted at a circumferentially offset position from the camera 16 so that the detector 20 does not receive light reflected by the mirror 22 from the light source 14 and/or laser 18.

The apparatus 10 also includes means for imparting vibrations, preferably ultrasonic vibrations, to the window 12 and the mirror 22. Conveniently, this comprises an ultrasonic transducer 24 comprising, in the preferred embodiment, a front or coupling mass 26, a back mass 28 and typically at least two piezoelectric transducers 30 (four shown in the drawings, although any other number may be used to achieve the desired intensity of vibration) sandwiched between the coupling mass 26 and the back mass 28. The coupling and back masses 26,28 may be formed from any suitable material, typically metal. It is preferred that the coupling mass 26 is formed from a corrosion resistant material, e.g. stainless steel, to limit the corrosive effects that the water sample in the chamber may otherwise have. The piezoelectric transducers 30 typically comprise ceramic, or piezo-ceramic elements or disks. During use, the ceramic transducers 30 convert electrical energy, supplied by an ultrasonic power supply unit, into mechanical energy which is imparted to the coupling and back masses 26,28 in conventional manner The window 12 and mirror 22 are mounted to resonate with the ultrasonic transducer, removing any fouling or contamination therefrom. The measurement window 12 is located within a recess in a front end of the coupling mass 26 and is held or clamped in place by a retaining ring 38. The measurement window 12 is held in contact with the end of the coupling mass 26 in order to impart ultrasonic vibrations thereto.

The mirror 22 comprises a stainless steel disc pressed out from a flat sheet to define a peripheral ring 40 adapted to be mounted between the outer face of the measurement window 12 and the retaining ring 38 and central mirror portion 42 connected to the peripheral ring 40 by a linking part 44. The central mirror portion 42 of the mirror 22 is positioned to reflect light from the light source/laser 14,18 towards the camera 16 and is mechanically coupled to the ultrasonic transducer 24 via the linking part 44 and peripheral ring 40 to keep the mirror clean.

The coupling mass 26 is provided with first, second and third channels for receiving, in the present embodiment, the camera 16, the light source 14 and laser 18, and the detector 20 respectively. The channels may be formed by, for example, appropriate machining of the coupling mass 26. The channels are non-parallel and converge in a direction towards the window 12.

Providing the laser source 18 in a respective channel is advantageous since it obviates the need to include an optical guide system to direct the laser light into the measurement chamber and so reduces the complexity of the apparatus 10 and eliminates the losses associated with optical guide systems. Similarly, by placing the free end of the light guide in a channel it is close to (preferably as close as possible to) the measurement window 12 and is therefore able to gather enough light to allow accurate measurements. This obviates the need to provide a more conventional optical guide system (typically including lenses and/or mirrors) for directing light out of the chamber and so eliminates losses associated with such optical guide systems.

Placing such components in close proximity with the ultrasonic transducer 24 would not conventionally be considered to be a design option because of the effects that the ultrasonic vibration can have on the components. In order to protect the components that are, in use, inserted into the channels from the effects of ultrasonic vibration, e.g. ultrasonic shock, it is preferred to line each respective channel with a vibration isolating sleeve 46 formed from any suitable material and may be rigid, semi-rigid or flexible. It is preferred that the sleeves 46 are formed from plastics, especially acetal plastics as, for example, provided under the trade name DELRIN by DuPont. Acetal, and similar material, provides high strength and resistance to impact and fatigue while having a limited impact on the ultrasonic transducer resonant frequency and dynamic performance.

The first and second channels, containing the camera 16 and light source/laser 14/18 respectively are preferably arranged in a common first plane extending through a longitudinal axis of the ultrasonic transducer, converging on the mirror 22, and said third channel, containing the fluorescence detector 20 is arranged in a second plane extending through said longitudinal axis of said ultrasonic transducer, said second plane being circumferentially offset from said first plane, said mirror being arranged to reflect light from the light source/laser 14/18 to the camera 16 in said first plane.

The ultrasonic transducer 24 is used, as required, to clean the measurement window 12 and mirror 22 and/or agitate or homogenise the water/oil in the measurement or sampling region defined between the window 12 and the mirror 22.

Ordinarily the provision of a mirror 22 would interfere with the operation of the laser when used as an excitation source for fluoroscopy. This is because it is not desirable for light from the laser to be reflected back towards the detector 20. The laser is only required to cause fluorescence in the oil. However, the respective position of each of the channels ensures that this does not happen.

The Sapphire window 12 is embedded within and is mechanically coupled with the ultrasonic transducer and thus conducts the energy produced by the transducer to create cavitations in the water in the sampling region, which in-turn cleans the window 12 and the mirror 22.

In an alternative embodiment illustrated in FIG. 4, the measurement window 12 is mounted perpendicular to the axis of the ultrasonic transducer and portions of the window 12 are shaped so that the light from the light source/laser 14/18 and the reflected light passing to the camera 16 passes through the window perpendicular to the surfaces of the window to avoid diffraction errors. Such may be achieved by cutting recesses into the faces of the window 12 in the regions through which light passes between the light source/laser 14/18 and the camera 16 via the mirror 22 so that the surfaces are perpendicular to the light passing therethrough.

The light source is mounted on the camera side of the sapphire window. The efficiency of the light transmitted through the sapphire window is maintained by the sonic/ultrasonic cavitations described above.

In an alternative embodiment of the present invention, illustrated in FIG. 5, the light source is provided on an opposite side of a measurement chamber 200 from the measurement head assembly 8 and light from the light source is directed directly towards the imaging camera 16 via a light guide assembly 202, comprising an elongate housing 204 extending into the measurement chamber within which is guided one or more optical cables or fibres 206 for guiding light from a remote light source (not shown) into the measurement chamber 200 through a terminal window 208 and towards the imaging camera 16. The light guide assembly 202 extends into the measuring chamber 200 to terminate adjacent the measurement window 12, thus providing effective back lighting of a sample located between the light guide 202 and the measurement window 12. The light guide assembly 202 may be arranged coaxially with the imaging camera 16 and perpendicular to the measurement window 12, as shown in FIG. 5, such that the optimum back lighting conditions are provided for the imaging camera 16 to provide an accurate image of any oil droplets located in the measurement region between the light guide assembly 202 and the measurement window 12.

In order to prevent fouling of the window 208 of the light guide 202, the light guide 202 terminates within the region of cavitation generated by the ultrasonic transducer 24 of the measurement head assembly such that the window 208 of the light guide 202 is exposed to said cavitation.

As with the first embodiment, the measurement head assembly 8 comprises an ultrasonic transducer 24 to which the measurement window 12 is mechanically coupled for keeping the window 12 clear and for propagating ultrasonic vibrations into the fluid sample adjacent the measuring window 12. The imaging camera 16 is mounted within a channel extending through a side of the ultrasonic transducer to view a fluid sample through the measurement window 12. An excitation source 18, in the form of a laser, and a detector (not shown in FIG. 5) are also incorporated into the measurement head assembly 8 for carrying out fluoroscopic analysis of the sample.

In an alternative embodiment (not shown) the light guide 202 may be omitted and a light source (e.g. an LED) may be mounted within the measurement chamber, light from said light source being directed through a window located in the region of cavitation generated by the ultrasonic transducer 24 of the measurement head assembly such that the window is exposed to said cavitation to prevent fouling of the window.

The invention is not limited to the embodiment(s) described herein but can be amended or modified without departing from the scope of the present invention.

The invention claimed is:

1. An in-line measurement apparatus for measuring fluorescent material and other bodies in a liquid flowing in a pipe, comprising:

measurement head assembly for sealably mounting in an opening in said pipe;

a generally cylindrical mass mounted in said measurement head assembly, said generally cylindrical mass having a coupling mass and a back mass;

a measurement window secured to a first end of said generally cylindrical mass with a retaining ring, a first side of said measurement window being in contact with said liquid in said pipe;

a light source in a light source opening in said first end of said generally cylindrical mass for shining a light through said measurement window into said liquid;

a mirror mounted with a linking part between said measurement window and said retaining ring, but inside said pipe, said mirror reflecting said light source shining through said measurement window to give a reflected signal;

a camera located in a camera opening in said first end of said generally cylindrical mass, said camera receiving said reflected signal via said measurement window;

transducers mounted between said coupling mass and said back mass on a second end of said generally cylindrical mass for mechanical coupling to said measurement window, said transducers causing vibrations of said measurement window and said mirror via said retaining ring and linking part and cavitations within a measurement region of said pipe, said vibrations and cavitations removing fouling from said measurement window and said mirror;

said measurement window being shaped so that said light from said light source and said reflected signal both hit surfaces of said measurement window at appropriately perpendicular angles.

2. The in-line measurement apparatus as recited in claim 1 wherein said light source is also an excitation source to cause fluorescent material to fluoresce.

3. The in-line measurement apparatus as recited in claim 2 includes a detector mounted in a detector cavity in said first end of said generally cylindrical mass, said detector being aimed at said measurement window to receive some of said reflected signal to detect fluoroscopy functions.

4. The in-line measurement apparatus as recited in claim 3 wherein a vibration isolating sleeve surrounds and protects said camera from said vibrations.

* * * * *